United States Patent [19]

Baldwin et al.

[11] 4,125,530

[45] Nov. 14, 1978

[54] TRIFLUOROMETHYLIMIDAZOLES AND A METHOD FOR THEIR PREPARATION

[75] Inventors: John J. Baldwin, Lansdale; Frederick C. Novello, Berwyn, both of Pa.

[73] Assignee: Merck & Co., Inc., Rahway, N.J.

[21] Appl. No.: 764,796

[22] Filed: Feb. 2, 1977

Related U.S. Application Data

[60] Continuation of Ser. No. 610,903, Sep. 5, 1975, abandoned, and a continuation-in-part of Ser. No. 455,709, Mar. 28, 1974, abandoned, which is a division of Ser. No. 265,016, Jun. 21, 1972, Pat. No. 3,818,014, which is a continuation-in-part of Ser. No. 885,362, Dec. 15, 1969, abandoned.

[51] Int. Cl.$^2$ .................. C07D 231/12; C07D 401/04
[52] U.S. Cl. .............................. 546/167; 260/306.8 R; 548/336; 548/341; 544/405; 544/235; 544/370; 546/210; 546/278

[58] Field of Search ............ 260/288 CE, 309, 302 H, 260/250 BN, 250 C, 296 R, 310 R; 548/336, 341

[56] References Cited

U.S. PATENT DOCUMENTS

| 3,652,579 | 3/1972 | Hofber et al. ........................ 260/309 |
| 3,691,178 | 9/1972 | Baldwin et al. ............... 260/288 CE |
| 3,786,061 | 1/1974 | Novello et al. ....................... 260/309 |
| 3,818,014 | 6/1974 | Baldwin et al. ............... 260/288 CE |

Primary Examiner—Donald G. Daus
Assistant Examiner—Mary C. Vaughn
Attorney, Agent, or Firm—Daniel T. Szura; Harry E. Westlake, Jr.

[57] ABSTRACT

4(5)-Trifluoromethylimidazoles having optional substituents in the 1 and 2 positions are provided. The novel 4(5)-trifluoromethylimidazoles are prepared by reacting a 1,1-dihalo-3,3,3-trifluoroacetone compound with an appropriate carboxaldehyde and ammonia. The 4(5)-trifluoromethylimidazoles are useful as anti-gout and anti-hyperuricemic agents.

6 Claims, No Drawings

TRIFLUOROMETHYLIMIDAZOLES AND A METHOD FOR THEIR PREPARATION

BACKGROUND OF THE INVENTION

This is a continuation of Ser. No. 610,903, filed Sept. 5, 1975, now abandoned, which in turn is a continuation-in-part of application Ser. No. 455,709, filed Mar. 28, 1974, now abandoned which in turn is a division of application Ser. No. 265,016, filed June 21, 1972 now U.S. Pat. No. 3,818,014, which in turn is a continuation-in-part of application Ser. No. 885,362 filed Dec. 15, 1969, now abandoned.

Field of the Invention

This invention relates to a class of chemical compounds which may be described as 4(5)-trifluoromethylimidazoles. These novel trifluoromethylimidazoles may be substituted in the 3 position by an alkyl group, an aryl group, or a heteroaryl group and in the 1 position by an alkyl group or an hydroxyalkyl group.

Description of the Prior Art

The herein-described 4(5)-trifluoromethylimidazoles have utility as anti-gout and anti-hyperuricemic agents.

Gout is a condition affecting humans and lower animals, particularly birds and reptiles, which is characterized by perversion of the purine metabolism resulting in an excess of uric acid in the blood, by attacks of acute arthritis, and by formation of chalky deposits in the cartilages of the joints. These deposits are made up chiefly of urates, or uric acid. Hyperuricemia is a condition characterized by an excess of uric acid in the blood.

Uric acid serves no biochemical function in the body and is merely an end product of purine metabolism. It is well known in the art that the purine bases adenine and guanine, which play key roles in a wide variety of chemical processes, both give rise to uric acid in the body. Adenylic acid and guanylic acid are converted to the free purine bases by destructive metabolic enzymes. A portion of the free purine bases is converted to purine ribonucleotides and the remainder is degraded to the free bases xanthine and hypoxanthine. A single enxyme, xanthine oxidase, converts both xanthine and hypoxanthine to uric acid for excretion.

Although human purine biosynthesis can be inhibited at the stage of formyl glycinimide ribotide by the glutamine antagonists azaserine and 6-diazo-5-oxo-1-norleucine, a high incidence of undesirable side effects precludes their being used clinically for this purpose. In recent years, substantial progress has been made in attempting to control the excessive levels of uric acid in patients afflicted with gout through the use of pharmaceutical agents. Uric acid synthesis has been effectively blocked by the use of allopurinol, 4-hydroxypyrazolo-[3,4-d]-pyrimidine, a compound which is a structural isomer of hypoxanthine. Allopurinol acts as a specific inhibitor of the enxyme xanthine oxidase, which is responsible for the conversion of both hypoxanthine and xanthine to uric acid. As a direct result of the administration of this compound to the patients afflicted with gout, part of the uric acid which would normally end up in the urine is replaced instead by the oxypurines, hypoxanthine and xanthine, thus greatly reducing the content of uric acid in serum and urine. Azathioprine has also been employed in patients afflicted by gout to inhibit the excessive purine synthesis, which tends to produce abnormal amounts of uric acid. Other compounds, such as acetylsalicylic acid, thiophenylpyrazolidine, and phenylbutazone have been employed in the treatment of gout. Many of the existing compounds used in the treatment of gout, however, relieve the inflammation and other symptoms connected therewith but have no effect on the conditions which give rise to gouty arthritis or hyperuricemia. Thus, there is still a need for compounds which can be employed in the prophylactic treatment of gout as well as for the treatment of other abnormal conditions associated with hyperuricemia.

SUMMARY OF THE INVENTION

An object of this invention is to provide novel 4(5)-trifluoromethylimidazoles which are useful in the treatment of gout and hyperuricemia. A second object of this invention is to describe products which have utility as hypotensive agents and products which are useful in the treatment of bronchoconstriction.

Still another object of this invention is to describe a method for preparing the herein disclosed products as, for example, by reacting a 1,1-dihalo-3,3,3-trifluoroacetone with an appropriate carboxaldehyde and ammonia.

Also, included within this invention are the nontoxic pharmaceutically acceptable quaternary salts and alkali metal and alkaline earth metal salts of the 4(5)-trifluoromethylimidazoles, and those acid salts wherein the substituent in the 2 position is a heterocyclic ring containing at least one nitrogen atom.

DESCRIPTION OF THE PREFERRED EMBODIMENTS:

The novel imidazoles which are the subject of the present invention can be structurally depicted as follows:

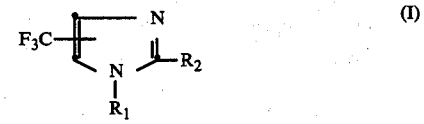

wherein
R$_1$ is hydrogen,
  lower alkyl wherein the alkyl group contains from 1-5 carbons such as methyl, ethyl, butyl and the like, or
  hydroxy lower alkyl such as 2-hydroxyethyl, 3-hydroxypropyl and the like; and
R$_2$ is hydrogen,
  methyl,
  lower alkyl having 3-5 carbons, such as n-butyl, propyl, n-pentyl, 2-methyl-n-butyl and the like,
  di-lower alkylamino-lower alkyl such as 2-dimethylaminoethyl or 1-dimethylamino-2-methyl-2-propyl and the like,
  an heterocycle selected from:
    pyridyl,
    pyridyl N-oxide,
    mono-alkyl and dialkyl substituted pyridyl, such as 2,6-dimethyl-4-pyridyl, 4,6-dimethyl-2-pyridyl, 2-methyl-3-pyridyl, 2-methyl-4-pyridyl or 6-methyl-3-pyridyl and the like,
    quinolyl,
    thiazolyl,
    furyl,
    thienyl,
    pyrazinyl, methoxy substituted pyrazinyl, 1-lower alkylpyrazolyl such as 1-methylpyrazolyl and the like, 1-mono-nuclear aryl substituted pyrazolyl wherein the aryl nucleus may be substituted by halo such as chloro, bromo, fluoro or iodo as, for example, 1-(4-chlorophenyl)-4-pyrazolyl and the like, or 1-mono-nuclear aralkyl substituted pyrazolyl such as 1-benzyl-4-pyrazolyl and the like, or mono-nuclear and binuclear aryl such as phenyl, naphthyl or substituted phenyl wherein the substituent is halo such as fluoro, bromo, chloro or iodo, cyano, carboxy, carboalkoxy wherein the alkoxy group contains from 1–5 carbons such as methoxycarbonyl, ethoxycarbonyl and butoxycarbonyl, lower alkyl wherein the alkyl group is a straight or branched chain group containing 1–5 carbon atoms, such as methyl, ethyl, propyl, butyl, isopropyl and pentyl, lower alkylidene wherein the alkylidene group contains from 2–5 carbons such as ethylidene, propylidene, butylidene and pentylidene, sulfamoyl, lower alkylsulfamoyl and di-lower alkylsulfamoyl wherein the alkyl group contains from 1–5 carbons, such as methylsulfamoyl, dimethylsulfamoyl, ethylsulfamoyl, butylsulfamoyl, and the like, lower alkoxy wherein the alkoxy group contains from 1–5 carbons such as methoxy, ethoxy, butoxy and the like, lower alkanoylamino wherein the alkyl group contains from 2–5 carbons such as acetylamino, propionylamino, butyrylamino and the like, nitro, amino, mono-lower alkylamino wherein the alkyl group contains from 1–5 carbons, such as methylamino, ethylamino and propylamino, di-lower alkylamino wherein the alkyl group contains from 1–5 carbons such as dimethylamino, diethylamino, dibutylamino, and the like, methylenedioxy, a fused lower alkylene chain containing from 3–6 carbons such as a propylene, butylene, or pentylene bridge, the residue formed by reaction of a cyclic anhydride, for example, maleic anhydride, with a primary or secondary aromatic amine wherein the amino moiety is on the 2-phenyl substituent as, for example, the maleamido moiety —NH—CO—CH=CH—COOH, trifluoromethyl substituted imidazolyl such as 4-trifluoromethyl-2-imidazolyl and the like, lower alkokymethyleneoxy such as methoxymethyleneoxy and the like, or di-lower alkylamino-lower alkoxy such as dimethylaminoethoxy or diethylaminoethoxy and the like.

Where the substituent on the imidazole ring is a substituted phenyl group, the phenyl ring may contain from 1–3 substitutents. Where the substituent on the phenyl ring is a lower alkylene bridge, the bridge is joined to the phenyl ring on adjacent carbons as, for example, by a 3, 4-propylene bridge. Where $R_2$ is a naphthyl group, the said naphthyl is joined to the imidazole ring at the 1 or 2 position of the naphthyl ring.

Where the substituent on the phenyl ring is methylenedioxy, the oxygen atoms are joined to the phenyl nucleus on adjacent carbons as, for example, at the 3 and 4 positions of the benzene ring.

Also within the scope of the present invention are the pharmaceutically acceptable quaternary salts such as the methiodides and ethiodides where the heterocyclic group in the 2 position contains a nitrogen atom, alkali metal and alkaline earth metal salts, such as the sodium, potassium and calcium salts, and those mineral acid salts such as the hydrochloride salts, wherein the substituent in the 2 position is a heterocyclic ring containing at least one nitrogen atom, such as a pyridine ring.

It should be understood that the 1-unsubstituted trifluoromethylimidazoles discussed herein are compounds in which the trifluoromethyl substituent is at either the 4 or 5 position on the imidazole ring. The hydrogen atom on a nitrogen in the imidazole ring is in a state of tautomeric equilibrium, with the result that the 4 and 5 positions are equivalent.

Typical of the compounds within the definition of Formula I and which are useful in the treatment of gout are, for example:

2-(4-pyridyl)-4(5)-trifluoromethylimidazole
1-methyl-2-(4-pyridyl)4-trifluoromethylimidazole
2-(4-thiazolyl)-4(5)-trifluoromethylimidazole
2-(2-furyl)-4(5)-trifluoromethylimidazole
1-ethyl-2-(4-thiazolyl)-4-trifluoromethylimidazole
2-isoamyl-4(5)-trifluoromethylimidazole
2-phenyl-4(5)-trifluoromethylimidazole
2-(o-cyanophenyl)-4(5)-trifluoromethylimidazole
2-(p-ethylphenyl)-4(5)-trifluoromethylimidazole
1-propyl-2-phenyl-4-trifluoromethylimidazole
2-vinylphenyl-4(5)-trifluoromethylimidazole
2-(p-sulfamoylphenyl)-4(5)-trifluoromethylimidazole
2-(p-N-methylsulfamoyl)-4(5)-trifluoromethylimidazole
1-methyl-2-(p-sulfamoylphenyl)-4-trifluoromethylimidazole
1-methyl-2-phenyl-5-trifluoromethylimidazole
2-(p-methoxyphenyl)-4(5)-trifluormethylimidazole
2-(6-quinolyl)-4(5)-trifluoromethylimidazole
2-(3-furyl)-4(5)-trifluoromethylimidazole
2-(2-thienyl)-4(5)-trifluoromethylimidazole
2-(3,4-methylenedioxyphenyl)-4(5)-trifluoromethylimidazole
2-(o-methoxyphenyl)-4(5)-trifluoromethylimidazole
2-(p-acetylaminophenyl)-4(5)-trifluoromethylimidazole
2-(p-cyanophenyl)-4(5)-trifluoromethylimidazole
1-methyl-2-(p-methoxyphenyl)-4-trifluoromethylimidazole
1-methyl-2-(p-methoxyphenyl)-5-trifluoromethylimidazole
2-(p-dimethylaminophenyl)-4(5)-trifluoromethylimidazole
2-(5-indanyl)-4(5)-trifluoromethylimidazole
2-(1-indanyl)-4(5)-trifluoromethylimidazole
2-(3,4-dichlorophenyl)-4(5)-trifluoromethylimidazole
2-(m-chlorophenyl)-4(5)-trifluoromethylimidazole
2-(p-fluorophenyl)-4(5)-trifluoromethylimidazole
1-methyl-2-(p-chlorophenyl)-4-trifluoromethylimidazole
2-(p-carboxyphenyl)-4(5)-trifluoromethylimidazole
2-(2-indanyl)-4(5)-trifluoromethylimidazole
2-(2-naphthyl)-4(5)-trifluoromethylimidazole
1-methyl-2-(p-acetylaminophenyl)-4-trifluoromethylimidazole and, 1-(2-hydroxyethyl)-2-(1-naphthyl)-5-trifluoromethylimidazole Those compounds wherein $R_1$ in Formula I is hydrogen, lower alkyl or hydroxy lower alkyl, and $R_2$ is 2-naphthyl, pyridyl, quinolyl, thiazolyl, furyl, thienyl, pyrazinyl and substituted phenyl wherein the substituent is said halo, cyano, carboxy, carboalkoxy, lower alkyl, sulfamoyl, lower alkoxy, lower alkanoylamino, nitro, amino, lower monoalkylamino, lower dialkylamino, methyleneoxy, a fused alkylene chain or the residue formed by reaction of a cyclic anhydride with an amine, represent a preferred sub-class of compounds within the scope of the present invention.

An especially preferred class of compounds are those of the following formula:

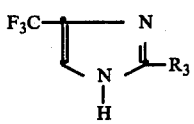

wherein $R_3$ is pyridyl such as 3-pyridyl or 4-pyridyl. As a whole, these products exhibit particularly good anti-gout and anti-hyperuricemic activity and constitute a preferred embodiment of this invention.

The products of this invention are effective anti-gout and anti-hyperuricemic agents in that they inhibit the action of the enzyme xanthine oxidase and thus reduce the content of uric acid in serum and urine.

In addition, the instant products (I) inhibit a random anti-hypertensive and bronchodilator effect.

Hypertension or high blood pressure is one of the most common of diseases affecting the heart and blood vessels. Aside from morbidity and mortality directly related to the presence of hypertension, the condition plays a prominent role in other cardiovascular diseases particularly coronary atherosclerosis and cerebrovascular disease. Patients with hypertension usually experience more congestive heart failure, hypertensive heart disease, hypertensive encephalopathy and renal failure than people who have normal blood pressure. And although various drugs are available for the treatment of hypertension, all have their limitations and deficiencies.

The ganglionic blocking agents cause postural hypotension, give poor control of supine blood pressure and cause dry mouth and paralysis of ocular accommodation along with other undesirable effects.

The sympathetic blocking agents are also limited in terms of response in patients due to the production of postural hypotension, fatigue, muscle aching, giddiness and diarrhea.

Furthermore, all patients will not respond to drugs that deplete or interfere with catecholamine metabolism. In addition, such drugs possess side effects that limit their usefulness. Thus, for example, hydralazine is limited due to its effect in causing tachycardia and immunologic reactions.

Also, the thiazide diuretics are useful in mild hypertension but in more severe cases must be used in combination with other agents since alone they are not effective. The thiazides also promote uric acid retention, hyperglycemia and potassium loss.

Due to the limitations and deficiencies of these agents, there is a medical need for a drug to replace them in the management of hypertension.

Those products which exhibit anti-hypertensive activity can be described as follows:

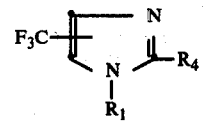

wherein $R_1$ is hydrogen or lower alkyl such as methyl, ethyl, propyl or n-butyl and the like, and $R_4$ is phenyl, halophenyl such as chlorophenyl or bromophenyl and the like, lower alkylphenyl such as tolyl or ethylphenyl and the like, pyridyl, lower alkylpyridyl such as 2-methyl-4-pyridyl or 6methyl-3-pyridyl and the like, pyridyl-N-oxide, thiazolyl, lower alkyl such as ethyl or isopropyl and the like, quinolyl, thienyl, di-arylmethyl such as diphenylethyl, lower alkanesulfonamidophenyl, such as methane-or ethanesulfonamidophenyl and the like, or (di-lower alkylaminoalkoxy)phenyl and the like, and the non-toxic pharmacologically acceptable acid addition salts and alkali metal salts thereof.

Illustrative of the products exhibiting this anti-hypertensive activity are, for example:

2-(3-pyridyl)-4(5)-trifluoromethylimidazole
2-(2-pyridyl)-4(5)-trifluoromethylimidazole
2-(4-pyridyl)-4(5)-trifluoromethylimidazole
2-(4-thiazolyl)-4(5)-trifluoromethylimidazole
2-isopropyl-4(5)-trifluoromethylimidazole
2-(2-thienyl)-4(5)-trifluoromethylimidazole
2-(o-chlorophenyl)-4(5)-trifluoromethylimidazole
2-(p-chlorophenyl)-4(5)-trifluoromethylimidazole
2-phenyl-4(5)-trifluoromethylimidazole
2-(p-methylsulfonamidophenyl)-4-trifluoromethylimidazole
2-(p-diethylaminoethoxyphenyl)4-trifluoromethylimidazole
2-(3-pyridyl-1-oxide)-4-trifluoromethylimidazole
2-diphenylmethyl-4-trifluoromethylimidazole
2-(1-methyl-4-pyrazolyl)-4-trifluoromethylimidazole
2-(2-methyl-4-pyridyl)-4-trifluoromethylimidazole
2-(6-methyl-3-pyridyl)-4-trifluoromethylimidazole
2-(6-quinolyl)-4(5)-trifluoromethylimidazole
1-methyl-2-phenyl-4-trifluoromethylimidazole, and
1-methyl-2-(p-chlorophenyl)-5-trifluoromethylimidazole The following products exhibit particularly good hypotensive activity:

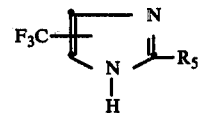

wherein $R_5$ is phenyl, halophenyl as, for example 3-iodophenyl, p-chlorophenyl and the like, pyridyl as, for example, 3-pyridyl or 4-pyridyl and the like, lower alkanesulfonamidophenyl as, for example, methanesulfonamidophenyl and the like or lower alkylpyridyl as, for example, 2-methyl-4-pyridyl or 6-methyl-3-pyridyl and the like. The above products and the non-toxic pharmacologically acceptable acid addition salts and alkali metal salts thereof are especially effective hypotensive agents and, therefore, constitute a preferred subclass of compounds within the scope of this invention.

The following products are also useful as bronchodilating agents. They are of significant value in the management of the asthmatic patient because they are useful as both prophylactic drugs and as adjuncts in the treatment of prolonged attacks and status asthmaticus. Any attack characterized by a decrease in vital capacity and an increase in residual air would be alleviated by the use of these agents:

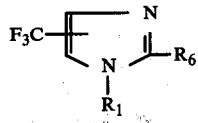

wherein $R_1$ is hydrogen or lower alkyl, such as methyl, ethyl, propyl and the like and $R_6$ is pyridyl, lower alkylpyridyl, such as methylpyridyl, ethylpyridyl and the like, thiazolyl, lower alkoxy substituted piperazinyl, such as methoxypiperazinyl and the like or piperidinyl substituted lower alkyl, such as piperidinyl substituted butyl and the like, and the non-toxic pharmacologically acceptable acid addition salts and alkali metal salts thereof.

The following subgroup of compounds exhibits particularly good bronchodilator activity:

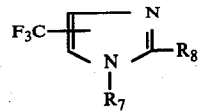

wherein $R_7$ and $R_8$ are methyl and pyridyl, respectively at the same time or, in the alternative, $R_7$ is hydrogen when $R_8$ is pyridyl, methylpyridyl, thiazolyl, or methoxy substituted piperazinyl. This subgroup of compounds is particularly useful in the treatment of bronchoconstriction and, therefore, constitutes a preferred embodiment of this invention.

The compounds of the present invention having the structural formula:

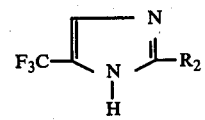

wherein $R_2$ is hydrogen, methyl,
lower alkyl, having 3–5 carbon atoms,
di-lower alkylamino-lower alkyl,
any of the heterocycles within the definition of $R_2$ supra, or
mono-nuclear and binuclear aryl such as phenyl, naphthyl
or substituted phenyl wherein the substituent is
halo,
cyano,
carboxy,
carboalkoxy,
lower alkyl,
lower alkylidene,
sulfamoyl,
lower alkylsulfamoyl,
lower alkoxy,
lower alkanoylamino,
nitro,
mono-lower alkylamino,
di-lower alkylamino,
methylenedioxy,
a fused lower alkylene bridge containing from 3–6 carbons,
trifluoromethyl substituted imidazolyl,
lower alkoxy-methyleneoxy or
di-lower alkylamino-lower alkoxy can be prepared by first reating a 1,1-dihalo-3,3,3-trifluoroacetone compound, such as 1,1-dibromo-3,3,3-trifluoroacetone, with mild base, such as sodium acetate, aqueous ammonia or potassium carbonate, and then reacting the basic mixture with the appropriate carboxaldehyde and ammonia. The carboxaldehyde may be an alkyl carboxaldehyde, such as acetaldehyde or propionaldehyde, an arylcarboxaldehyde, such as benzenecarboxaldehyde, a substituted arylcarboxaldehyde, such as o-cyanobenzenecarboxaldehyde, p-nitrobenzenecarboxaldehyde, p-sulfamoylbenzenecarboxaldehyde, and p-methoxybenzenecarboxaldehyde, or a heteroarylcarboxaldehyde, such as pyridinecarboxaldehyde, quinolinecarboxaldehyde, thiazolecarboxaldehyde, thiophenecarboxaldehyde, or cinnolinecarboxaldehyde.

The overall reaction scheme can be depicted as follows:

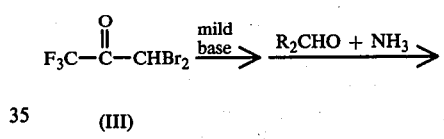

(III)

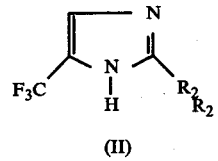

(II)

For example, where $R_2$ in Formula II is 4-pyridyl, the trifluoromethylimidazole compound is prepared by reacting about equimolar amounts of, for example, 1,1-dibromo-3,3,3-trifluoroacetone with 4-pyridinecarboxaldehyde and ammonia. In general, the trifluoroacetone compound is first added to a solution containing a slight excess of a mild base; any mild base, such as sodium acetate or potassium carbonate, may be employed. Hydroxylic solvents such as aqueous ethanol or water may be employed, but the reaction is generally carried out in water. The solution is heated for from about 5 minutes to about 2 hours at a temperature between room temperature and about 150° C.; the preferred temperature range, however, is about 80°–100° C. The reaction is then cooled, preferably to ice bath temperatures. The cooled solution is then added to a solution of the carboxaldehyde in a suitable solvent. Water-miscible solvents such as methanol, ethanol, dioxane or tetrahydrofuran may be employed. Ammonia is then added to the reaction mixture, and the mixture is allowed to stand at about room temperature for from about 1 – 10 hours. The ammonia may be added as a gas or alternatively as an aqueous or alcoholic solution. The trifluoromethylimidazole compound is then obtained by techniques known in the art. For example, concentration of the reaction mixture will generally yield the trifluoromethylimidazole compound as a solid residue. The product can be purified by recrystallization from an appropriate solvent such as water, acetonitrile or benzenehexane.

Those compounds wherein the substituent on the phenyl ring is amino can be prepared from the 2-phenyltrifluoromethylimidazole compounds having loweralkanoylamino group as the substituent on the phenyl ring. The reaction is carried out by first suspending a loweralkanoylaminophenyltrifluoromethylimidazole compound such as, for example, 2-(p-acetylaminophenyl)-4(5) -trifluoromethylimidazole, in a dilute mineral acid such as, for example, 10% hydrochloric acid, and the acid suspension is heated for from about 15 minutes to about two hours at a temperature of about 50° - 150° C. The preferred temperature range is 75° - 100° C. The aminophenyltrifluoromethylimidazole compound is obtained by neutralizing the acid solution with a mild alkali such as sodium bicarbonate and collecting the resulting precipitate by techniques known in the art. Alternatively, the 2-aminophenyltrifluoromethylimidazol compounds can be obtained by catalytic reduction of the corresponding nitro compounds.

Those compounds wherein the substituent in the 2-position is the residue formed by reaction of a cyclic anhydride with an amino can be prepared from a 2-aminophenyl-4(5)-trifluoromethylimidazole by reacting the 2-aminophenyl-4(5trifluoromethylimidazole compound with maleic anhydride in a suitable solvent such as, for example, diethyl ether. The reaction is generally carried out at room temperature, but temperatures between room temperature and about 50° C. may be employed. The reaction product generally crystallizes from the reaction mixture and is collected and purified by techniques known in the art.

The compounds of Formula I wherein $R_1$ is lower alkyl can be prepared by reacting a 4(5)-trifluoromethylimidazole such as, for example, 2-(p-fluorophenyl)-4(5)trifluoromethylimidazole, with an alkylating agent such as diazomethane or with a di-lower alkylsulfate such as dimethylsulfate in a suitable solvent such as acetic acid or methanol, or with a lower alkylhalide such as methyliodide in a suitable solvent, as, for example, in a mixture of toluene and dimethylsulfoxide. The alkylation may be carried out at room temperature, but it is preferred to carry out the reaction at elevated temperatures from about 10°-⅛° C. for from about 1-30 hours. The reflux temperature of the solvent is a convenient temperature for the alkylation step. The alkylated trifluoromethylimidazole compound is then isolated by techniques known in the art. For example when the alkylating agent is a di- lower alkylsulfate, one such method of isolation consists in removing the solvent and triturating the residue with dilute alkali, such as ammonium hydroxide, followed by the taking up of the product in a suitable solvent such as hexane. The alkylated trifluoromethylimidazole compound is then obtained upon removal of the solvent.

Those compounds of Formula I where R is hydroxy-lower alkyl can be prepared by reacting a 1,2-epoxy or 1,3-epoxy loweralkane, such as, for example, 1,2-epoxyethane and 1,3-epoxypropane, with about an equimolar mixture of a 4-(5)-trifluoromethylimidazole compound and a Lewis acid, in a suitable solvent, such as acetic acid or methyl alcohol. As the Lewis acid, compounds such as boron trifluoride and sulfur trioxide can be employed. Generally, a molar excess of the epoxide is employed, and the reaction is carried out at a temperature between about -40° C. and 60° C. The preferred reaction temperature, however, is between about 20° C. and 50° C. The epoxide is usually added gradually at such a rate as to keep the reaction within the desired temperature range. Depending upon the temperature range employed, the reaction mixture is allowed to stand from about 10 minutes to about 18 hours. The hydroxy-alkylated 4(5)-trifluoromethylimidazole compound is then isolated by techniques known in the art.

In order to prepare those compounds of Formula I wherein $R_1$ is hydroxyloweralkyl, it may be necessary in some instances to protect the compounds having substituents which are sensitive to the alkylating agents in order to obtain a good yield.

Where the substituent on the 2-phenyl substituent is a carboxy group, the carboxy group can be protected by converting it to the ester. Where the phenyl substituent is substituted with an amino group or a monoalkyl amino group, the amine function can be protected by acylation with, for example, an acetyl group. Where the substituent on the 2-phenyl substituent is a diamino group, the amino function can be protected by converting it to an N-oxide. Where the substituent on the 2-phenyl substituent is a sulfamoyl group, the sulfamoyl group may also be alkylated. The sulfamoyl group can be regenerated by reaction with chlorosulfonic acid, followed by reaction of the resulting sulfonyl chloride compound with ammonia. In those cases where a protecting group is necessary, the protecting group is removed by techniques known in the art.

The quaternary salts which fall within the scope of the present invention have as the substituent in the 2-position a nitrogen-containing aromatic ring such as a pyridine or quiniline ring. These quaternary salts can be prepared by reacting the 2- substituted 4(5)-trifluoromethylimidazole compound with an alkyl iodide such as, for example, methyl iodide or ethyl iodide in a suitable solvent, such as methanol, ethanol, or dimethyformamide. The reaction is generally carried out at room temperture, and the quaternary salt is usually obtained as a solid upon removal of the solvent. The following are examples of quaternary salts which are within the scope of the present invention:

N-methyl-4-[4(5)-trifluoromethyl-2-imidazolyl-]pyridinium iodide

N-ethyl-4-[4-(5)-trifluoromethyl-2-imidazolyl]-quinolinium iodide

N-methyl-2-(1 -ethyl-4-trifluoromethyl-2-imidazolyl)-pyridinium iodide, and

N-methyl-3-[1-(2-hydroxyethyl-4-trifluoromethyl-2-imidazolyl)]-pyridinium iodide.

The metal salts of the 4(5)-trifluoromethylimidazoles, that is, those compounds where $R_1$ in Formula I is hydrogen, can be prepared by methods known in the art. For example, the sodium or potassium salt can be prepared by addition of an equivalent amount of sodium or potassium hydroxide to a solution of the trifluoromethylimidazole compound. The salt is then obtained by concentrating the reaction mixture.

The acid addition salts of the 4(5)-trifluoromethylimidazoles having in the 2-position a heterocyclic ring containing at least one nitrogen atom can be prepared by any of the known methods for preparing acid addition salts of amines.

The 4(5)-trifluoromethylimidazoles which are the subject of this invention inhibit the action of the enzyme xanthine oxidase resulting in a significant decrease in the concentration of uric acid in the blood and urine and are, therefore, capable of aborting attaks of gout.

In addition, as indicated above, some of the 4(5)-trifluoromethylimidazoles, such as 2-(3-pyridyl)-4(5)-trifluoromethylimidazole and 2-(4-pyridyl)-4(5)-trifluoromethylimidazole exhibit hypotensive activity and also inhibit gastric secretion.

For testing purposes, xanthine oxidase obtained from milk may be employed to demonstrate the ability of the 4(5)-trifluoromethylimidazoles to inhibit the enzyme. The general procedure is to employ a 5–10 unit suspension of the enzyme per milliliter of 60% saturated ammonium sulfate of the enzyme; 1 unit of such as suspension converts 1$\mu$ mole of xanthine to uric acid per minute. Generally, for a 1-day assay, about 0.05 ml. of enzyme is diluted with about 3 ml. of buffer. As the buffer, tris buffer (0.05 mole) pH 7.4 may be employed. The inhibitor to be tested is dissolved in buffer or a suitable solvent, such as dimethylsulfoxide; the same solvent is used to dilute the solution. The buffer, hypoxanthine and solvent are placed in a cell, and the resulting solution is shaken to absorb air. The diluted enzyme solution is then added, and the rate of increase in absorbance at 290 m$\mu$ is noted with a recording spectrophotometer. Generally, sufficient enzyme is employed to give about 0.1 absorbance units change per minute, and sufficient inhibitor is used to give 30–70% inhibition. The $\mu$M concentration of inhibitor necessary for 50% inhibition ($V_O/V_1 = 2$) is determined by plotting $V_O/V_1$ against I, where $V_O$ = velocity without inhibitor, $V_1$ = velocity with inhibitor, and I = inhibitor concentration. The activity of the tested compound is expressed in terms of percent inhibition.

The therapeutically active trifluoromethylimidazoles can be administered as the active ingredient in association with a pharmaceutically acceptable carrier in the form of tablets, elixirs, capsules, and the like. These preparations may be made by any of the known pharmaceutical methods. For example, in tablet form, they are compounded with an inert pharmaceutical carrier which may contain a suitable binder such as, for example, gums, starches, and sugars. They may also be incorporated into a gelatin capsule or formulated into elixirs which have the advantage of being susceptible to manipulations in flavor by the addition of standard natural or synthetic flavoring materials, The compound is generally administered in compositions which are so proportioned as to afford a unit dosage of about 30 mg to 1.5 gm. per day. The preferred dosage level, however, is about 100–800 mg. per day.

The following examples serve to illustrate typical tablet, capsule, and elixir formulations incorporating the therapeutically active 4(5)-trifluoromethylimidazoles of this invention.

FORMULATION I: COMPRESSED TABLET COMPRISING 0.5 GM. OF ACTIVE INGREDIENT

FORMULATION I:

| COMPRESSED TABLET COMPRISING 0.5 GM. OF ACTIVE INGREDIENT | |
|---|---|
| Ingredient | Amount - Mg. |
| 2-(4-pyridyl)-(4)-trifluoromethyl-imidazole | 500.0 |
| Starch paste - 12½%, 100 cc. allow. | 12.5 |
| | 512.5 |
| Starch, USP Corn | 25.0 |

FORMULATION I:-continued

| COMPRESSED TABLET COMPRISING 0.5 GM. OF ACTIVE INGREDIENT | |
|---|---|
| Ingredient | Amount - Mg. |
| Magnesium stearate | 5.5 |
| | 543.0 |

The 2-(4-pyridyl)-4(5)-trifluoromethylimidazole is granulated with the starch paste and while moist passed through a No,. 14 screen, dried at 45° C. for 20 hours, and then passed 3 times through a No. 14 screen. The starch is then passed through a No. 90 bolting cloth onto the granulation, and all ingredients are blended thoroughly. The magnesium stearate is passed through a No. 90 bolting cloth onto the granulation, and these ingredients are blended, after which the granulation is compressed into tablets using a 14/32" flat, bevelled, scored punch having a thickness of 0.205± 0.005" yielding 1,000 tablets each weighing 0.543 grams.

FORMULATION II: ENCAPSULATION - FOR 250 MG. CAPSULE

FORMULATION II:

| ENCAPSULATION - FOR 250 MG. CAPSULE | |
|---|---|
| Ingredient | Amount - Mg. |
| 2-(6-quinolyl)-4(5)-trifluoromethyl-imidazole | 250 |
| Lactose | 93 |
| Talc | 7 |

Blend lactose, talc and the 2-(6-quinolyl)-4(5)-trifluoromethylimidazole in suitable blending equipment, and encapsulate into a No. 2 capsule at a target weight of 350 mg.

FORMULATION III: LIQUID SUSPENSION - FORMULA

FORMULATION III:

| LIQUID SUSPENSION - FORMULA | |
|---|---|
| Ingredient | Amount - g./l. |
| Veegum H.V. | 3.0 |
| Water | 150.0 |
| Methyl Paraben | 1.0 |
| 2-(p-carboxyphenyl-4(5)-trifluoromethyl-imidazole | 50.0 |
| Kaolin | 10.0 |
| Flavor | 1.0 |
| Glycerin, 9.5 to 1 liter | |

Suspend Veegum in water with vigorous agitation, add methyl paraben and allow to stand overnight to ensure complete hydration of Veegum. In separate vessel suspend 2-(p-carboxyphenyl)-4(5)-trifluoromethylimidazole in about 750 cc. of glycerol. Add kaolin and stir until homogeneous. Slowly add aqueous dispersion of Veegum and methyl paraben. Add flavor and continue agitation for 1 hour to ensure homogeneity. Q.S. with remaining glycerin to 1:1. Stir until homogeneous. 1 Teaspoonful contains 250 mg. of 2-(p-carboxyphenyl)-4(5)-trifluoromethylimidazole.

The following examples are given for purposes of illustration and not by way of limitation:

EXAMPLE 1

2-(4-PYRIDYL)-4(5)-TRIFLUOROMETHYLIMIDAZOLE

Sodium acetate trihydrate (11.6 grams, 0.084 mole) is dissolved in 40 ml. of water, and 1,1-dibromo-3,3,3-trifluoroacetone (11.6 grams, 0.042 mole) is added to the resulting aqueous solution. The solution is heated for 30 minutes at 100° C. and is then cooled in an ice bath. The cooled solution is added to a solution of 4-pyridinecarboxaldehyde (4.7 grams, 0.044 mole) in methanol (200 ml.). Concentrated aqueous ammonia (50 ml.) is added to the alcoholic solution, and the reaction mixture is allowed to stand for 5 hours at room temperature. The mixture is then concentrated to about 75 ml., and the product separates from the solution as an oil which solidifies on standing. Upon recrystallization from water, there is obtained 2-(4-pyridyl)-4(5)-trifluoromethylimidazole, m.p. 156°–157.5° C.

When in the above procedure 3-pyridinecarboxaldehyde is employed in place of 4-pyridinecarboxaldehyde, there is obtained 2-(3-pyridyl)-4(5)-trifluoromethylimidazole, m.p. 228°–228.5° C.

When in the above procedure 2-pyridinecarboxaldehyde is employed in place of 4-pyridinecarboxaldehyde, there is obtained 2-(2-pyridyl)-4(5)-trifluoromethylimidazole, m.p. 156°–157.5° C.

The procedure described in Example 1 is used to prepare the following compounds (Examples 2 – 28):

EXAMPLES 2–33

| Ex. No. | (0.044 mole) Starting Material | Product | Melting Point |
|---|---|---|---|
| 2 | 2-quinoline-carboxaldehyde | 2-(2-quinolyl)-4(5)-trifluoromethylimidazole | 156.5–158° C. |
| 3 | 4-thiazole-carboxaldehyde | 2-(4-thiazolyl)-4(5)-trifluoromethyl-imidazole | 235–236° C |
| 4 | 2-furan-carboxaldehyde | 2-(2-furyl)-4(5)-tri-fluoromethylimidazole | 192–193.5° C. |
| 5 | isobutyraldehyde | 2-isopropyl-4(5)-tri-fluoromethylimidazole | 201.5–202.5° C. |
| 6 | methylimidazole aldehyde | 2-isobutyl-4(5)-trifluoro-methylimidazle | 123°–125° C. |
| 7 | acetaldehyde | 2-methyl-4(5)-trifluoro-methylimidazole | 161–165° C. |
| 8 | formaldehyde | 4(5)-trifluoromethyl-imidazole | 148.5–149.5° C. |
| 9 | 1-naphthylene-carboxaldehyde | 2-(1-naphthyl)-4(5)-trifluoromethylimidazole | 249–250° C. |
| 10 | 2-naphthylene-carboxaldehyde | 2-(2-naphthyl)-4(5)-trifluoromethylimidazole | 210–211° C. |
| 11 | 2-thiophene-carboxaldehyde | 2-(2-thienyl)4-(5)-tri-fluoromethylimidazole | 211.5–212° C. |
| 12 | p-cyanobenzene-carboxaldehyde | 2-(p-cyanophenyl)-4(5)-trifluoromethylimidazole | 207–208° C. |
| 13 | p-fluorobenzene-carboxaldehyde | 2-(p-fluorophenyl)-4(5)-trifluoromethylimidazole | 206.5–207.5° C. |
| 14 | o-chlorobenzene-carboxaldehyde | 2-(o-chlorophenyl)-4(5)-trifluoromethylimidazole | 165–167° C. |
| 15 | m-chlorobenzene-carboxaldehyde | 2-(m-chlorophenyl)-4(5)-trifluoromethylimidazole | 186.5–187.5° C. |
| 16 | p-chlorobenzene-carboxaldehyde | 2-(p-chlorophenyl)-4(5)-trifluoromethylimidazole | 226–228° C. |
| 17 | 3,4-dichloro-benzenecarbox-aldehyde | 2-(3,4-dichlorophenyl)-4(5)-trifluoromethyl-imidazole | 212.5–213.5° C. |
| 18 | 2,4-dichloro-benzene-carboxaldehyde | 2-(2,4-dichlorophenyl)-4(4)-trifluoromethyl-imidazole | 191–193° C. |
| 19 | p-carboxybenzene-carboxaldehyde | 2-(p-carboxyphenyl)-4(5)-trifluoromethyl-imidazole | 287° C. dec. |
| 20 | p-methylbenzene-carboxaldehyde | 2-(p-methylphenyl)-4(5)-trifluoromethylimidazole | 218–220° C. |
| 21 | m-methylbenzene-carboxaldehyde | 2-(m-methylphenyl)-4(5)-trifluoromethylimidazole | 190–191° C. |
| 22 | p-sulfamoyl-benzenecarbox-aldehyde | 2-(p-sulfamoylphenyl)-4(5)-trifluoromethyl-imidazole | 290° C. dec. |
| 23 | 5-indane carboxaldehyde | 2-(5-indanyl)-4(5)-trifluoromethyl-imidazole | 211–213° C. |
| 24 | benzenecarbox-aldehyde | 2-phenyl-4(5)-tri-fluoromethylimidazole | 208–209.5° C. |
| 25 | p-methoxybenzene-carboxaldehyde | 2-(p-methoxyphenyl)-4(5)-trifluoromethyl-imidazole | 204–206° C. |
| 26 | p-acetylamino-benzenecarbox-aldehyde | 2-(p-acetylamino-phenyl)4-(5)-tri-fluoromethylimidazole | 273–274° C. |
| 27 | p-nitrobenzene-carboxaldehyde | 2-(p-nitrophenyl)-4(5)-trifluoro-methylimidazole | 195–196.5° C. |
| 28 | p-dimethyl-aminobenzene-carboxaldehyde | 2-(p-dimethylamino-phenyl)-4(5)-tri-fluoromethylimidazole | 264–265° C. |
| 29 | 3,4-methylene-dioxybenzene-carboxaldehyde | 2-(3,4-methylenedioxy-phenyl)-4(5)-trifluoro-methylimidazole | 204–207° C. |
| 30 | m-bromobenzene-carboxaldehyde | 2-(m-bromophenyl)-4(5)-trifluoro-methylimidazole | 189° C. |
| 31 | 3-methoxy-pyrazine-carboxaldehyde | 2-[2(5-methoxy-pyrazinyl)]-4(5)-trifluoromethyl-imidazole | 218–220° C. |

EXAMPLES 2-33-continued

| Ex. No. | (0.044 mole) Starting Material | Product | Melting Point |
|---|---|---|---|
| 32 | p-isopropyl-benzenecarbox-aldehyde | 2-(p-isopropyl-phenyl)-4(5)-tri-fluoromethylimidazole | 249° C. |
| 33 | 6-quinolinecarbox-aldehyde | 2-(6-quinolyl)-4(5)-trifluoromethylimidazole | 254.5-255° C. |

EXAMPLE 34

2-(p-AMINOPHENYL)-4(5)-TRIFLUOROMETHYLIMIDAZOLE 2-(p-Acetamidophenyl)-4(5)-trifluoromethylimidazole (4 grams) is suspended in 10% hydrochloric acid (85 ml.), and the suspension is heated at 100° C. for about 30 minutes. The resulting solution is filtered, and the filtrate is neutralized with aqueous sodium bicarbonate. The crude product settles out of the neutral solution, and after recrystallization from benzene, 2-(p-aminophenyl)-4(5)-trifluoromethylimidazole, m.p. 214.5°-215° C., is obtained.

EXAMPLE 35 p-[4(5)-TRIFLUOROMETHYL-2-IMIDAZOLYL]-MALEANILIC ACID 2-(p-Aminophenyl)-4(5)-trifluoromethylimidazole (1.13 grams, 0.005 mole) is dissolved in ether (150 ml.). A solution of maleic anhydride (0.5 grams, 0.005 mole) in ether (50 ml.) is added to the resulting solution, and the resulting solution is allowed to stand for one hour at room temperature. The product settles out of solution and is collected by filtration. Additional crystals are obtained upon concentration of the ether filtrate. The combined solids are dissolved in 2.5% aqueous sodium hydroxide and re-precipitated by the addition of hydrochloric acid. Upon filtration and recrystallization from 70% ethanol, there is obtained p-[4(5)-trifluoromethyl-2-imidazolyl]-maleanilic acid, m.p. 235.5°-237° C.

EXAMPLE 36

2-(3,4-DIMETHOXYPHENYL)-4(5)-TRIFLUOROMETHYLIMIDAZOLE

Sodium acetate trihydrate (0.084 mole) is dissolved in 50 ml. of water, and 1,1-dibromo-3,3,3-trifluoroacetone (0.042 mole) is added to the resulting aqueous solution. The solution is heated for 25 minutes at 95° C. and is then cooled in an ice bath. The cooled solution is added to a solution of 3,4-dimethoxybenzenecarboxaldehyde (0.044 mole) in methanol (175 ml.). Concentrated aqueous ammonia (50 ml.) is added to the alcoholic solution, and the reaction mixture is allowed to stand for 5 hours at room temperature. The mixture is then concentrated to about 75 ml., and the product separates from the solution as an oil which solidified on standing. Upon recrystallization from alcohol, there is obtained 2-(3,4-dimethoxyphenyl)-4(5)-trifluoromethylimidazole, m.p. 188°-190° C.

When in the above procedure p-N,N-dimethylsulfamoylbenzenecarboxaldehyde and p-methylaminobenzenecarboxaldehyde are employed in place of 3,4-dimethoxybenzenecarboxaldehyde, there are obtained 2-(p-N,N-dimethylsulfamoylphenyl)-4(5)-trifluoromethylimidazole and 2-(p-methylaminophenyl)-4(5)-trifluoromethylimidazole, respectively.

EXAMPLE 37

When in Example 1 2,6-dimethyl-4-pyridinecarboxaldehyde, 4,6-dimethyl-2-pyridinecarboxaldehyde, and 2-methyl-3-pyridinecarboxaldehyde are employed in place of 4-pyridinecarboxaldehyde, there are obtained 2-(2,6-dimethyl-4-pyridyl)-4(5)-trifluoromethylimidazole, 2-(4,6-dimethyl-2-pyridyl)-4(5)-trifluoromethylimidazole, and 2-(2-methyl-3-pyridyl)-4(5)-trifluoromethylimidazole, respectively.

EXAMPLE 38

N-METHYL-4[4(5)-TRIFLUOROMETHYL-2-IMIDAZOLYL]-PYRIDINIUM IODIDE

To a solution of 2-(4-pyridyl)-4(5)-trifluoromethylimidazole (2.13 grams, 0.01 mole) in methanol (50 ml.) is added methyl iodide (7 grams, 0.05 mole). The resulting solution is allowed to stand for 24 hours at room temperature, and the solvent is concentrated until a solid is obtained. The solid is washed with diethyl ether and is collected by filtration, yielding 2.4 grams of crude product. Upon recrystallization from isopropyl alcohol, N-methyl-4[4(5)-trifluoromethyl-2-imidazolyl]-pyridinium iodide is obtained, m.p. 230°-232° C., dec.

When in the above procedure ethyl iodide is employed in place of methyl iodide, N-ethyl-4]4(5)-trifluoromethyl-2-imidazolyl]-pyridinium iodide is obtained.

EXAMPLE 39

2-(p-FLUOROPHENYL)-1-METHYL-4(AND 5)-TRIFLUOROMETHYLIMIDAZOLE

Dimethylsulfate (0.63 grams, 0.005 mole) is added to a solution of 2-(p-fluorophenyl)-4(5)-trifluoromethylimidazole (1.1 grams, 0.005 mole) in acetic acid (10 ml.), and the reaction mixture is refluxed overnight. After 17 hours at reflux, additional dimethylsulfate (0.63 grams, 0.005 mole) is added, and the solution is heated at reflux for an additional 5 hours. The acetic acid is removed in vacuo, and the resulting residue is triturated with dilute ammonium hydroxide, water, and then with hexane. The hexane extract is concentrated to a solid residue and is sublimed to yield 200 mg. of product. Upon recrystallization from hexane, 2-(p-fluorophenyl)-1-methyl-4(5)-trifluoromethylimidazole are obtained, m.p. 81°-84.5° C. Thin layer chromatography and VPC indicate the presence of two isomeric components.

When in the above procedure diethylsulfate is employed in place of dimethylsulfate, 2-(p-fluorophenyl)-1-ethyl-4(and 5) -trifluoromethylimidazole are obtained.

EXAMPLE 40

1-(2-HYDROXYETHYL)-5-TRIFLUOROMETHYLIMIDAZOLE

4(5)-Trifluoromethylimidazole (0.062 mole) is dissolved in 150 ml. of acetic acid, and boron trifluoride etherate (0.057 mole) is added to the resulting solution.

Ethylene oxide (0.35 mole) in 20 ml. of hexane is added dropwise with stirring during one hour to the reaction mixture while maintaining the temperature of the reaction mixture at 32°–35° C. wit a water bath. After the addition of ethylene oxide is complete, the mixture is concentrated in vacuo to about 20 ml., and the residue is diluted with 50 ml. of water neutralized to pH 7 with aqueous sodium hydroxide and extracted with 100 ml. of ethyl acetate. The extract is dried over magnesium sulfate and filtered. Upon removal of the solvent, 1-(2-hydroxyethyl)-5-trifluoromethylimidazole is obtained.

When in the above procedure 2-(o-chlorophenyl)-4(5)-trifluoromethylimidazole and 2-(p-methylphenyl)-4(5)-trifluoromethylimidazole are employed in place of 4(5)-trifluoromethylimidazole, there are obtained 1-(2-hydroxyethyl)-2-(o-chlorophenyl)-5-trifluoromethylimidazole and 1-(2-hydroxyethyl)-2-(p-methylphenyl)-5-trifluoromethylimidazole, respectively.

EXAMPLE 41

2-PYRAZINYL-4(5)-TRIFLUOROMETHYLIMIDAZOLE

Sodium acetate trihydrate (5.8 g., 0.042 mole) is dissolved in 20 ml. of water, and 1,1-dibromo-3,3,3-trifluoroacetone (5.8 g., 0.021 mole) is added to the resulting aqueous solution. The solution is heated for 30 minutes at 100° C., and is then cooled in an ice bath. The cooled solution is added to a solution of 2-pyrazinecarboxaldehyde (2.3 g., 0.022 mole) in methanol (100 ml.). Concentrated aqueous ammonia (25 ml.) is added to the alcoholic solution, and the reaction mixture is allowed to stand for 5 hours at room temperature. The mixture is then concentrated to about 35 ml., and the product separates from the solution as an oil which solidifies on standing. Upon recrystallization from acetonitrile, there is obtained 2-pyrazinyl-4(5)-trifluoromethylimidazole, m.p., 237°–238° C.

EXAMPLE 42

2-(p-METHYLSULFONAMIDOPHENYL)-4-TRIFLUOROMETHYLIMIDAZOLE

To a solution of 2-(p-aminophenyl)-4-trifluoromethylimidazole (3.0 g.) in acetone (50 ml.) and triethylamine (2.7 g.) is added methanesulfonyl chloride (1.5 g.). After refluxing for 4 hours, a second portion of methanesulfonyl chloride (1.5 g.) is added. Reflux is continued 20 hours, a third portion of methanesulfonyl chloride (1.5 g.) is added and reflux continued another 4 hours. The reaction mixture is filtered and concentrated to an oil which, upon trituration with water, affords a solid. After chromatography on silica gel and recrystallization from a mixture of acetonitrile and water 1.3 g. of 2-(p-methylsulfonamidophenyl)-4-trifluoromethylimidazole, m.p. 253–255° C. is obtained.

EXAMPLE 43

1,4-BIS(4-TRIFLUOROMETHYL-2-IMIDAZOLYL)BENZENE

To a solution of sodium acetate trihydrate (5.9 g.) in water (20 ml.) is added 1,1-dibromo-3,3,3-trifluoroacetone (5.9 g., 0.022 mole). The solution is heated 45 minutes at steam bath temperature and then cooled. The solution is added to a solution of terephthalaldehyde (1.34 g., 0.01 mole) in methanol (100 ml.) and concentrated aqueous ammonia (25 ml.). The reaction mixture is allowed to stand for 4 hours at room temperature. The reaction mixture is concentrated under reduced pressure; water is added and the resulting solid is filtered. After recrystallization from a mixture of methanol and water 450 mg. of 1,4-bis(4-trifluoromethyl-2-imidazolyl)benzene, m.p. 325° C., is obtained.

EXAMPLE 44

2-(1-DIMETHYLAMINO-2-METHYL-2-PROPYL)-4-TRIFLUOROMETHYLIMIDAZOLE

To a solution of sodium acetate trihydrate (11.8 g.) in water (40 ml.) is added 1,1-dibromo-3,3,3-trifluoroacetone (11.8 g., 0.044 mole). The solution is heated 45 minutes at steam bath temperature and then cooled. The solution is added to a solution of 2,2-dimethyl-3-dimethylaminopropionaldehyde (5.6 g., 0.044 mole) in methanol (150 ml.) and concentrated aqueous ammonia (50 ml.). The reaction mixture is allowed to stand for 3.5 hours at room temperature and the reaction mixture is then concentrated under reduced pressure to yield a semi-solid which is recrystallized from hexane and then sublimed to yield 3 g. of 2-(1-dimethylamino-2-methyl-2-propyl)-4-trifluoromethylimidazole, m.p., 133–135° C.

EXAMPLE 45

2-(m-METHOXYMETHOXYPHENYL)-4-TRIFLUOROMETHYLIMIDAZOLE

To a solution of sodium acetate trihydrate (11.8 g.) in water (40 ml.) is added 1,1-dibromo-3,3,-trifluoroacetone (11.8 g., 0.044 mole). The solution is heated 45 minutes at steam bath temperature and then cooled. The solution is added to a solution of m-methoxymethoxybenzaldehyde (7.2 g., 0.004 mole) in methanol (300 ml.) and concentrated aqueous ammonia (50 ml.). The reaction mixture is allowed to stand 4.5 hours at room temperature. The reaction mixture is concentrated under reduced pressure to yield an oil which solidifies. After recrystallization from a mixture of benzene and hexane 4.1 g. of 2-(m-methoxymethoxyphenyl)-4-trifluoromethylimidazole m.p., 155.5°–157.5° C. is obtained.

EXAMPLE 46

2-(p-DIETHYLAMINOETHOXYPHENYL)-4-TRIFLUOROMETHYLIMIDAZOLE

To a solution of sodium acetate trihydrate (5.9 g.) in water (20 ml.) is added 1,1-dibromo-3,3,3-trifluoroacetone (5.9 g., 0.022 mole). The solution is heated 60 minutes at steam bath temperature and then cooled. The solution is added to a solution of p-diethylaminoethoxybenzaldehyde (2.4 g., 0.011 mole) in methanol (100 ml.) and concentrated aqueous ammonia (25 ml.). The reaction mixture is allowed to stand 4 hours at room temperature. The reaction mixture is concentrated under reduced pressure and extracted with ether. The ether extract is dried and concentrated to an oil which after chromatography on silica gel and recrystallization form a mixture of ethanol and water gave 0.6 g. of 2-(p-diethylaminoethoxyphenyl)-4-trifluoromethylimidazole, m.p., 145°–146° C.

EXAMPLE 47

2-(3-PYRIDYL-1-OXIDE)-4-TRIFLUOROMETHYLIMIDAZOLE

To a solution of 2-(3-pyridyl)-4-trifluoromethylimidazole (1.0 g.) in acetic acid (10 ml. ) is added 30% hydrogen peroxide (1 g.). The reaction mixture is heated overnight at steam bath temperature and is poured onto 10 ml. of saturated aqueous sodium bicarbonate solution. The mixture is neutralized with 40% aqueous sodium hydroxide and the resulting solid is filtered and recrystallized from water to yield 250 mg. of 2-(3-pyridyl-1-oxide)-4-trifluoromethylimidazole, m.p. 224°–225° C.

By substituting 2-(4-pyridyl)-4-trifluoromethylimidazole for 2-(3-pyridyl)-4-trifluoromethylimidazole in the above method and otherwise following the procedure described therein there is thus obtained 2-(4-pyridyl-1-oxide)-4-trifluoromethylimidazole, m.p., 242° C.

EXAMPLE 48

2-(1-BENZYL-4-PYRAZOLYL)-4-TRIFLUOROMETHYLIMIDAZOLE

To a solution of sodium acetate trihydrate (5.9 g.) in water (20 ml.) is added 1,1-dibromo-3,3,3-trifluoroacetone (5.9 g., 0.022 mole). The solution is heated 45 minutes at steam bath temperature and then cooled. The solution is added to a solution of 1-benzyl-4-pyrazolecarboxaldehyde (3.6 g., 0.02 mole) in methanol (75 ml.) and concentrated aqueous ammonia (25 ml.). The reaction mixture is allowed to stand 4.5 hours at room temperature. The mixture is concentrated to afford an oil which, on trituration with hexane, gives a solid. After recrystallization from benzene 0.7 g. of 2-(1-benzyl-4-pyrazolyl)-4-trifluoromethylimidazole, m.p., 157°–159.5° C., is obtained.

EXAMPLE 49

2-DIPHENYLMETHYL-4-TRIFLUOROMETHYLIMIDAZOLE

To a solution of sodium acetate trihydrate (5.8 g.) in water (20 ml.) is added 1,1-dibromo-3,3,3-trifluoroacetone (5.9 g., 0.022 mole). The solution is heated 60 minutes at steam bath temperature and then cooled. The solution is added to a solution of 1,1-diphenylacetaldehyde (4.3 g., 0.022 mole) in methanol (150 ml.) and concentrated aqueous ammonia (25 ml.). The reaction mixture is allowed to stand for five hours at room temperature. The reaction mixture is concentrated under reduced pressure to half volume, water is added and the solid removed by filtration. After recrystallization from a mixture of acetonitrile and water 2.0 g. of 2-diphenylmethyl-4-trifluoromethylimidazole, m.p., 230°–231° C. is obtained.

EXAMPLE 50

2-(1-PHENYL-4-PYRAZOLYL)-4-TRIFLUOROMETHYLIMIDAZOLE

To a solution of sodium acetate trihydrate (2.9 g.) in water (10 ml.) is added 1,1-dibromo-3,3,3-trifluoroacetone (2.9 g., 0.011 mole). The solution is heated 45 minutes at steam bath temperature and then cooled. The solution is added to a solution of 1-phenyl-4-pyrazolecarboxaldehyde (1.7 g., 0.01 mole) in methanol (50 ml.) and concentrated aqueous ammonia (15 ml.). The reaction mixture is allowed to stand for four hours at room temperature. The mixture is concentrated under reduced pressure and the resulting solid is filtered. After recrystallization from acetonitrile 0.6 g. of 2-(1-phenyl-4-pyrazolyl)-4-trifluoromethylimidazole, m.p., 205°–206° C., is obtained.

EXAMPLE 51

2-(1-METHYL-4-PYRAZOLYL)-4-TRIFLUOROMETHYLIMIDAZOLE

To a solution of sodium acetate trihydrate (2.7 g.) in water (10 ml.) is added 1,1-dibromo-3,3,3-trifluoroacetone (2.7 g., 0.01 mole). The solution is heated 45 minutes at steam bath temperature and then cooled. The solution is added to a solution of 1-methyl-4-pyrazolecarboxaldehyde (1.1 g., 0.01 mole) in methanol (50 ml.) and concentrated aqueous ammonia (15 ml.). The reaction mixture is allowed to stand for 4.5 hours at room temperature. The mixture is concentrated and the resulting product is chromatographed on silica gel and recrystallized from water to yield 100 mg. of 2-(1-methyl-4-pyrazolyl)-4-trifluoromethylimidazole, m.p. 206°–207° C.

EXAMPLE 52

2-[1-(p-CHLOROPHENYL)-4-PYRAZOLYL]-4-TRIFLUOROMETHYLIMIDAZOLE

To a solution of sodium acetate trihydrate (10.0 g.) in water (35 ml.) is added 1,1-dibromo-3,3,3-trifluoro-acetone (10.0 g., 0.037 mole). the solution is heated 30 minutes at steam bath temperature and then cooled. The solution is added to a solution of 1-(p-chlorophenyl)pyrazole-4-carboxaldehyde (7.8 g., 0.038 mole) in methanol (140 ml.) and concentrated aqueous ammonia (43 ml.) The reaction mixture is allowed to stand 4.5 hours at room temperature. The reaction mixture is concentrated under reduced pressure and the resulting product is recrystallized from a mixture of water and acetonitrile to yield 2.64 g. of 2-[1-(p-chlorophenyl)-4-pyrazolyl]-4-trifluoromethylimidazole, m.p., 233°–235° C.

EXAMPLE 53

2-(2-METHYL-4-PYRIDYL)-4-TRIFLUOROMETHYLIMIDAZOLE

To a solution of sodium acetate trihydrate (5.8 g.) in water (20 ml.) is added 1,1-dibromo-3,3,3-trifluoroacetone (5.9 g., 0.022 mole). The solution is heated 45 minutes at steam bath temperature and then cooled. The solution is added to a solution of 2-methylisonicotinaldehyde (2.4 g., 0.02 mole) in methanol (100 ml.) and concentrated aqueous ammonia (25 ml.). The reaction mixture is allowed to stand 4.5 hours at room temperature. The reaction mixture is concentrated under reduced pressure; an oil separates and solidifies and this is filtered (0.6 g.) after recrystallization from a mixture of water and ethanol to afford 2-methyl-4-pyridyl)-4-trifluoromethylimidazole, m.p., 195°–197° C.

EXAMPLE 54

2-(6-METHYL-3-PYRIDYL)-4-TRIFLUOROMETHYLIMIDAZOLE

To a solution of sodium acetate trihydrate (8.7 g.) in water (30 ml.) is added 1,1-dibromo-3,3,3-trifluoroacetone (8.7 g., 0.032 mole). The solution is heated 30 minutes at steam bath temperature and then cooled. The solution is added to a solution of 6-methylnicotinaldehyde (3.6 g., 0.03 mole) in methanol (150 ml.) and concentrated aqueous ammonia (37 ml). The reaction mixture is allowed to stand for four hours at room temperature. The reaction mixture is concentrated under reduced pressure and the resulting solid is filtered. After recrystallization from acetonitrile 2.1 g. of 2-(6-methyl-3-pyridyl)-4-trifluoromethylimidazole, m.p., 243° C., is obtained.

EXAMPLE 55

1-METHYL-2-(3-PYRIDYL)-4-TRIFLUOROMETHYLIMIDAZOLE

To 2-(3-pyridyl)-4(5)-trifluoromethylimidazole (2.1g.) in 15 ml. of toluene-dimethylsulfoxide (9:1) is added 57% sodium hydride in mineral oil (0.46 g.). The mixture is stirred for 15 minutes at room temperature; methyl iodide (1.6 g.) is added and stirring is continued for three hours. The reaction mixture is filtered; the solid portion is washed with benzene and the combined filtrate concentrated to an oil. The oil is distilled in an evaporative still at 165° C. and 0.3 mm. pressure. The distillate is chromatographed on silica gel to yield essentially pure 1-methyl-2-(3-pyridyl)-4-trifluoromethylimidazole which is redistilled in an evaporative still at 165° C. and 0.3 mm. to afford 0.8 of product.

Analysis for $C_{10}H_8F_3N_3$. calculated: N, 18.50; C, 52.86; H, 3.55. Found: N, 18.25; C, 52.92; H, 3.65.

EXAMPLE 56

1-METHYL-2-(2-PYRIDYL)-4-TRIFLUOROMETHYLIMIDAZOLE

To 2-(2-pyridyl)-4(5)-trifluoromethylimidazole (2.1 g.) in 15 ml. of toluene-dimethylsulfoxide (9:1) is added 57% sodium hydride in mineral oil. After stirring for 15 minutes at room temperature, methyl iodide (1.6 g.) is added. The reaction mixture is stirred four hours and filtered; the solid portion is washed with benzene and the combined filtrates are concentrated to an oil which solidifies. After recrystallization from hexane 250 mg. of 1-methyl-2-(2-pyridyl)-4-trifluoromethylimidazole, m.p., 78°–80° C., is obtained.

Analysis for $C_{10}H_8F_3N_3$. Calculated: N, 18.50; C, 52.86; H, 3.55. Found: N, 18.36; C, 52.77; H, 3.58.

EXAMPLE 57

1-METHYL-2-PHENYL-4-TRIFLUOROMETHYLIMIDAZOLE

By substituting an equivalent amount of 2-phenyl-4-trifluoromethylimidazole for the 2-(2-pyridyl)-4(5)-trifluoromethylimidazole of Example 57 and following substantially the procedure described therein there is obtained 250 mg. of 1-methyl-2-phenyl-4-trifluoromethylimidazole, m.p., 61.5°–62.5° C.

Analysis for $C_{11}H_9F_3N_2$. Calculated: C, 58.41; H, 4.01; N, 12.39. Found: C, 58.82; H, 4.02; N, 12.44.

EXAMPLE 58

1-ETHYL-2-PHENYL-4-TRIFLUOROMETHYLIMIDAZOLE

By substituting equivalent amounts of ethyl iodide and 2-phenyl-4-trifluoromethylimidazole for the methyl iodide and 2-(2-pyridyl)-4(5)-trifluoromethylimidazole of Example 57 and following substantially the procedure described therein there is obtained 1-ethyl-2-phenyl-4-trifluoromethylimidazole, b.p., 160°–165° C. at 0.5 mm.

Analysis for $C_{12}H_{11}F_3N_2$. Calculated: C, 59.97; H, 4.62; N, 11.66. Found: C, 59.91; H, 4.53; N, 11.45.

EXAMPLE 59

1-METHYL-2-(4-PYRIDYL)-4-TRIFLUOROMETHYLIMIDAZOLE

By substituting an equivalent amount of 2-(4-pyridyl)-4(5)-trifluoromethylimidazole for the 2-(2-pyridyl)-4(5)-trifluoromethylimidazole of Example 57 and following substantially the procedure described therein there is obtained 0.75 g. of 1-methyl-2-(4-pyridyl)-4-trifluoromethylimidazole, m.p., 125°–126.5° C.

EXAMPLE 60

1-METHYL-2-PHENYL-5-TRIFLUOROMETHYLIMIDAZOLE

To a solution of 2-phenyl-4(5)-trifluoromethylimidazole (4.2 g.) in acetic acid (40 ml.) is added dimethylsulfate (5.0 g.) and the mixture is heated at reflux for 16 hours. Dimethylsulfate (2.5 g.) is added and reflux is continued for 8 hours. The reaction mixture is concentrated to an oil and saturated aqueous sodium bicarbonate is added whereupon a solid separates. The solid is treated with hexane and insoluble material is removed. The hexane solution is then concentrated to a solid and chromatographed and recrystallized from hexane to afford 30 mg. of 1-methyl-2-phenyl-5-trifluoromethylimidazole, m.p., 118°–120° C.

Analysis for $C_{11}H_9F_3N_2$. Calculated: C, 58.41; H, 4.01; N, 12.39. Found: C, 58.50; H, 3.97; N, 12.26.

EXAMPLE 61

1-METHYL-2-(p-CHLOROPHENYL)-5-TRIFLUOROMETHYLIMIDAZOLE

To a solution of 2-(p-chlorophenyl)-4(5)-trifluoromethylimidazole (3.7 g.) in acetic acid (30 ml.) is added dimethylsulfate (5 g.) and the mixture is heated for 16 hours on a steam bath. Dimethylsulfate (2.0 g.) is added and heating is continued for 8 hours. Again dimethylsulfate (2.0 g.) is added and heating continued for 64 hours. The reaction mixture is concentrated to an oil and 10% aqueous sodium hydroxide is added until neutral. The solid which separates is filtered, recrystallized from hexane and distilled in an evaporative still in 170° C. and 0.3 mm. pressure to yield 1-methyl-2-(p-chlorophenyl)-5-trifluoromethylimidazole, m.p., 62°–67° C.

Analysis for $C_{11}H_8ClF_3N_2$. Calculated: C, 50.69; H, 3.09; N, 10.75. Found: C, 50.82; H, 3.07; N, 10.61.

EXAMPLE 62

1-METHYL-2-(2-PYRIDYL)-4-AND-5-TRIFLUOROMETHYLIMIDAZOLE

An ethereal solution of diazomethane (3.0 g., 0.07 mole) is added with cooling to a solution of 2-(2-pyridyl)-4(5)-trifluoromethylimidazole (6.5 g., 0.03 mole) in ether (200 ml.). After standing overnight at room temperature the reaction solution is concentrated to a dark oil, from which the product is extracted with boiling hexane. Concentration of the hexane and distillation of the crude product at 86° C. and 0.2 mm. mercury yields 2.7 g. of pure 1-methyl-2-(2-pyridyl)-4-and-5-trifluoromethylimidazole, m.p., 42°–49° C. Vapor phase chromatography shows an 88%–12% mixture of the 4-and-5-trifluoromethyl substituted products.

EXAMPLE 63

1-METHYL-2-(4-PYRIDYL)-4-AND-5-TRIFLUOROMETHYLIMIDAZOLE

An ethereal solution of diazomethane (4.5 g., 0.107 mole) is added with cooling to a solution of 2-(4-pyridyl)-4-(5)-trifluoromethylimidazole (10.0 g., 0.047 mole) in ether (200 ml.) and methanol (25 ml.). After standing overnight at room temperature the precipitated solid is filtered and the filtrate is concentrated to a viscous oil which is extracted with boiling hexane. On standing a solid separates and this material is filtered and recrystallized from water to yield 1-methyl-2-(4-pyridyl)-4-trifluoromethylimidazole (930 mg.), m.p., 122°–124° C. The hexane filtrate is then concentrated to a solid and after recrystallization from hexane yields 1-methyl-2-(4-pyridyl)-5-trifluoromethylimidazole (610 mg.), m.p., 50°–52° C.

EXAMPLE 64

1-METHYL-2-PHENYL-4-AND-5-TRIFLUOROMETHYLIMIDAZOLE

An ethereal solution of diazomethane (3.0 g., 0.07 mole) is added with cooling to a solution of 2-phenyl-4(5)-trifluoromethylimidazole (6.4 g., 0.03 mole) in ether (200 ml.) and methanol (15 ml.). After standing overnight at room temperature the reaction solution is concentrated to a solid and this material is extracted with boiling hexane. Concentration of the hexane extract yields crude product which is purified by column chromatography and recrystallization from hexane to yield 1-methyl-2-phenyl-4-trifluoromethylimidazole and 1-methyl-2-phenyl-5-trifluoromethylimidazole (430 mg.), m.p., 107°–112° C. Vapor phase chromatography shows an 83%–17% mixture of isomers.

EXAMPLE 65

2-(6-QUINOLYL)-4(5)-TRIFLUOROMETHYLIMIDAZOLE

To a solution of sodium acetate trihydrate (5.8 g.) in water (20 ml.) is added dibromotrifluoroacetone (5.8 g.). The resulting solution is heated 0.5 hours on a steam bath cooled and added to quinoline-6-carboxaldehyde (3.4 g.) in methanol (100 ml.) and concentrated aqueous ammonia (25 ml.). The reaction mixture is allowed to stand for 6 hours at room temperature and the methanol is then removed under reduced pressure. Water (25 ml.) is added whereupon a solid separates and this material is filtered and recrystallized from acetonitrile to yield 1.3 g. of 2-(6-quinolyl)-4(5)-trifluoromethylimidazole, m.p. 254.5°–255° C.

Analysis for $C_{13}H_8F_3N_3$. Calculated: C, 59.32; H, 3.06; N, 15.96. Found: C, 59.61; H, 3.00; N, 16.07.

Upon substituting quinoline-4-carboxaldehyde for the quinoline-6-carboxaldehyde in the above method and otherwise following the procedure described therein, there is thus obtained 2-(4-quinolyl)-4(5)-trifluoromethylimidazole at m.p. 206°–207° C.

Analysis for $C_{13}H_8F_3N_3$. Analysis for $C_{13}H_8F_3N_3$. Calculated: C, 59.32; H, 3.06; N, 15.96; F, 21.66. Found: C, 59.77; H, 3.16; N, 16.19; F, 21.36.

EXAMPLE 66

2-(1-PIPERIDINO-2-METHYL-2-PROPYL)-4(5)-TRIFLUOROMETHYLIMIDAZOLE

To a solution of sodium acetate trihydrate (11.8 g.) in water (40 ml.) is added dibromotrifluoroacetone (11.8 g.). The resulting solution is heated 0.5 hours on a steam bath, cooled and added to 3-piperidino-2,2-dimethylpropionaldehyde (7.5 g.) in methanol (20 ml.) and concentrated aqueous ammonia (50 ml.). The reaction mixture is allowed to stand for 4.5 hours at room temperature and the methanol is then removed under reduced pressure. Water (50 ml.) is added whereupon a solid separates and this material is filtered and recrystallized from hexane to yield 1.8 g. of 2-(1-piperidino-2-methyl-2-propyl)-4(5)-trifluoromethylimidazole, m.p. 113.5°–115.5° C.

Analysis for $C_{13}H_{20}F_3N_3$. Calculated: N, 15.26; C, 56.71, H, 7.32. Found: N, 15.09; C, 56.39; H, 7.09.

It should be understood that although this invention has been described with reference to particular embodiments thereof, changes and modifications may be made which are within its intended scope, and it should be limited only by the language of the appended claims.

What is claimed is:

1. A process for preparing a compound of the formula:

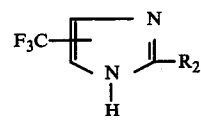

wherein $R_2$ is
hydrogen,
methyl,
$C_3$-$C_5$ alkyl,
2-dimethylaminoethyl,
1-dimethylamino-2-methyl-2-propyl,
pyridyl,
pyridyl-N-oxide,
monomethylpyridyl,
dimethylpyridyl,
6-quinolyl,
2-quinolyl,
3-quinolyl,
4-quinolyl,
pyrazinyl,
methoxypyrazinyl,
4-chlorophenyl-4-pyrazolyl,
4-thiazolyl,
phenyl,
o-cyanophenyl,
p-ethylphenyl,
p-sulfamoylphenyl,
p-N-methylsulfamoylphenyl,
p-methoxyphenyl,
3-furyl,
2-thienyl,
o-methoxyphenyl,
p-acetylaminophenyl,
p-cyanophenyl,
p-dimethylaminophenyl,
5-indanyl,
1-indanyl,
3,4-dichlorophenyl,
p-carboxyphenyl,
2-indanyl,
2-naphthyl,
1-naphthyl,
monohalophenyl,
p-methylsulfonamidophenyl, p-diethylaminoethoxyphenyl,
diphenylmethyl,
1-methyl-4-pyrazolyl,
p-nitrophenyl,
2-aminophenyl,
2-furyl,
2,4-dichlorophenyl,
p-carboxyphenyl,
monomethylphenyl,
3,4-methylenedioxyphenyl,
p-isopropylphenyl,
3,4-dimethoxyphenyl,
p-N,N-dimethylsulfamoylphenyl,
p-methylaminophenyl,
2,6-dimethyl-4-pyridyl,
4,6-dimethyl-2-pyridyl,
pyrazinyl,
m-methoxymethoxyphenyl,
p-diethylaminoethoxyphenyl,
1-benzyl-4-pyrazolyl,
1-phenyl-4-pyrazolyl,
1-methyl-4-pyrazolyl, and
1-piperidino-2-methyl-2-propyl which comprises the steps of
  (a) treating 1,1-dihalo-3,3-trifluroacetone with a base and then
  (b) treating the resulting mixture with ammonia and the appropriate carboxaldehyde.

2. The process of claim 1 wherein the product thus obtained is treated with 1,2-epoxyethane or 1,3-epoxypropane in the presence of a Lewis acid to afford the corresponding 1-hydroxyalkyl-4(5)-trifluoromethylimidazole.

3. The process according to claim 1 wherein $R_2$ is said naphthyl, alkyl, quinolyl, thiazolyl, furyl, thienyl, pyrazinyl or substituted phenyl group.

4. The process of claim 1 wherein 1,1-dibromo-3,3,3-trifluoroacetone is treated with sodium acetate trihydrate at 80°–100° C., and the resulting mixture is treated with 2,3,4-or 6- quinolinecarboxaldehyde and ammonia to afford the corresponding 2-(quinolyl)-4(5)-trifluoromethylimidazole.

5. The process of claim 1 wherein 1,1-dibromo-3,3,3-trifluoroacetone is treated with sodium acetate trihydrate at 80°–100° C., and the resulting mixture is treated with p-chlorobenzenecarboxaldehyde and ammonia to afford 2-(p-chlorophenyl)-4(5)-trifluoromethylimidazole.

6. The process of claim 1 wherein 1,1-dibromo-3,3,3-trifluoroacetone is treated with sodium acetate trihydrate at 80°–100° C, and the resulting mixture is treated with 4-thiazolecarboxaldehyde and ammonia to afford 2-(4-thiazolyl)-4(5)-trifluoromethylimidazole.

* * * * *